United States Patent [19]

Ferraris et al.

[11] 4,197,420

[45] Apr. 8, 1980

[54] METHOD FOR PRODUCING OLIGOMERS FROM STRAIGHT-CHAIN ALPHA OLEFINS, SUBSEQUENTLY HYDROGENATING SUCH OLIGOMERS AND SATURATED PRODUCTS SO OBTAINED

[76] Inventors: Giuseppe Ferraris; Aldo Priola; Sebastiano Cesca, all of San Donato Milanese, Italy

[21] Appl. No.: 911,921

[22] Filed: Jun. 2, 1978

[30] Foreign Application Priority Data

Jul. 18, 1977 [IT] Italy ................................ 25811 A/77

[51] Int. Cl.² ................................................ C07C 3/21
[52] U.S. Cl. ...................................... 585/522; 585/10; 585/255; 585/329

[58] Field of Search .................. 260/676 R, 683.15 D, 260/683.9; 585/10, 255, 329, 522

[56] References Cited

U.S. PATENT DOCUMENTS 4,017,553   4/1977   Cesca et al. ................ 260/683.15 D Primary Examiner—C. Davis
Attorney, Agent, or Firm—Morgan, Finnegan, Pine, Foley & Lee

[57] ABSTRACT

Oligomers are obtained from straight-chain alpha olefins by contacting these with a catalytic system of the binary type, which is composed of an organic metallic compound of aluminum and a haloid acid. Subsequent hydrogenation of the oligomers is carried out in order to remove possible residual unsaturations.

27 Claims, No Drawings

METHOD FOR PRODUCING OLIGOMERS FROM STRAIGHT-CHAIN ALPHA OLEFINS, SUBSEQUENTLY HYDROGENATING SUCH OLIGOMERS AND SATURATED PRODUCTS SO OBTAINED

This invention relates to a method for the production of oligomers starting from alpha-olefins coming from the several distillation cuts of the cracking products of higher hydrocarbons, to the subsequent hydrogenation of such oligomers and also to the saturated oligomeric products thus obtained.

It is known that the paraffin oils in recent times have found a wide number of applications in the food industry, in the pharmaceutical industry, in agriculture, as diluents for pest-control agents, rubber extenders, plasticizers and lubricant oils.

The paraffin oils are generally obtained by refining appropriate fractions of crude oil. However, the situation which has arisen recently with respect to the shortage in crude supplies and the considerable price increases have made such refining processes in the production of paraffin oils somewhat unattractive and disadvantageous.

An alternative route towards the obtaining of such oils is the cationic oligomerization of the alpha olefins which contain, predominantly, from 3 to 6 carbon atoms, the oligomerization being conductive to the formation of oily products having a low mol weight and containing residual unsaturation in the chain. these residual unsaturations can be removed by a hydrogenation process to form a saturated product.

However, the conventional hydrogenation methods, which are primarily based on the use of Friedel-Crafts halides, exhibit a number of shortcomings, such as low reaction yields, difficulties in the control of the reaction conditions and thus an uneasy performance of the reaction.

It has now been ascertained, and this is a first feature of the present invention, that a method for the preparation of oligomers from alpha-olefins which utilizes a special catalyst system has the advantages, over conventional procedures, of resulting in higher polymer yields, easier performance of the process and a more easily controllable reaction, the reaction system being, moreover, wholly homogeneous.

By means of the catalytic system of the present invention, it becomes possible to prepare oligomers from alpha-olefins in which the number is carbon atoms of from 3 to 12, and especially oligomers of propylene, butene-1, pentene-1 and hexene-1.

The catalytic system of the invention is composed of two components, selected from compounds among the following classes of compounds: (a) an organic metallic compound of aluminum, as represented by the following general formula:

$$R_mAlX_{3-m}$$

wherein X is a halogen atom, R is hydrogen or a monovalent radical, such as a alkyl, a aryl, a cycloalkyl, a aralkyl, a alkaryl, alkoxy or an ester radical having from 1 to 12 carbon atoms, and m is a number between 1 and 3, and (b) a compound capable of reacting with the compounds of the class (a) to give the catalytic species capable of initiating polymerization and having the formula HX, wherein X is a halogen.

Examples of compounds of class (a) are $AlEtCl_2$, $AlEt_2Cl$, $AlEt_{1.5}Cl_{1.5}$ and others.

Examples of compounds of class (b) are HCl, HBr, HF, HI.

The reaction is carried out in a homogeneous phase and in the presence of a solvent which is selected, as a rule from, among hydrocarbons or halogen-substituted hydrocarbons having from 3 to 12 carbon atoms. It is possible, nevertheless, to operate without a solvent, the solvent phase being in such a case the excess of the monomer present. The two components of the catalytic system can be introduced into the reaction medium either simultaneously or separately and the order of addition has no significant bearing on the catalytic species which can be obtained.

The molar ratio of the compound (a) to the component (b) may be between 0.1 and 5 to 1.0, the preferred range being from 0.5 to 3 to 1.0.

The reaction is conducted at a temperature in a range between $-30°$ C. and $+100°$ C., the preferred range being from $-10°$ C. to $+80°$ C.

The products which are obtained from the polymerization have a number average mol wt of from 200 to 3000 and contain residual unsaturations which can be expressed in terms of bromine number (i.e. grams of Br absorbed by 100 g of polymer), which is determined according to any of several methods, such as, for example, ASTM D 1159.

The unsaturation which are left on completion of the oligomerization can be either reduced or removed completely by a hydrogenation step, which is another feature of this invention, and which is carried out at a temperature between 150° C. and 300° C., under partial hydrogen pressures between 20 atm and 150 atm, in the presence of a hydrogenation catalyst such as Ni on kieselguhr, Ni-Raney, Pd on charcoal, Pt on charcoal.

Possible trace residues of unsaturated products (the Br number of the treated product being below 0.1) can eventually be removed by flowing the oligomeric compounds through adsorbing siliceous earths at a temperature between 50° C. and 100° C., to give the saturated products which are another feature of the present invention.

The foregoing and the operational details will become more clearly apparent from the ensuing illustrative examples which are not to be construed as limitations to this invention.

EXAMPLE 1

A 100 ml steel autoclave having a magnetic stirrer and a thermometer well, and which has previously been dried in a vacuum, is charged, by siphoning thereinto a solution containing 1.5 millimols of anhydrous HCl diluted in 1 ml of nor.pentane and 14 g of a C4 hydrocarbon cut having the following composition:

| | |
|---|---|
| Propane | 1.22% |
| Propylene | 0.29% |
| Isobutane | 3.68% |
| Nor.butane | 17.08% |
| Butene-1 | 61.64% |
| Butene-2-trans | 10.30% |
| Butene-2-cis | 2.15% |
| Isobutene | 3.64% |

The temperature is stabilized to $+20°$ C., whereafter there is introduced, by nitrogen overpressure, a solution containing 1.5 millimol of AlEtCl$_2$ diluted in 10 mls of nor.pentane (Molar ratio of HCl to AlEtCl$_2$=1.0).

A temperature rise up to 28° C. is experienced. The reaction is continued for 30 mins and is then discontinued by addition of methanol.

The unreacted monomers are flashed and the resultant product is washed with water supplemented with NaOH to remove the traces of the catalyst and subsequently washed with distilled water until neutrality is attained.

The hydrocarbonaceous phase is then evaporated to dryness to remove the solvent completely. There are obtained 7.85 g of dry oligomer (yield 85.9% calculated with respect to butene-1 and isobutene which are present) which has an average osmometric mol wt, $\overline{Mn}$, of 592 and a content of unsaturations, expressed in terms of Br number, of 38.5, as determined according to the method ASTM D 1159, and a content of residual Cl$_2$ of 1144 ppm (parts per million) as determined with an X-ray fluorescence apparatus. Simultaneously, with the same procedure, a sample test is carried out by introducing in the autoclave the same quantities of C$_4$ hydrocarbon fraction and then introducing 1.5 millimols of AlEtCl$_2$. A temperature increase of 1.5° C. (from +21° C. to 22.5° C.) is experienced and, after discontinuation of the reaction, there is obtained 0.35 g (yield 4.0%) of polymer on which it is not been possible to determine any property.

The product obtained by using the catalytic system AlEtCl$_2$ plus HCl is subjected to hydrogenation in order to remove the unsaturations present in the polymeric chain by following the procedure indicated hereinafter. An autoclave having a mechanical stirrer and a thermometer well is charged with 5.0 g of product and 0.34 g of Ni Raney prepared according to the procedures reported in A.I. Vogel, Practical Organic Chemistry, Longmans, Green & Co. Ed. page 870 (1956). The temperature is brought to 270° C. with a hydrogen pressure of 90 atm for a period of 20 hrs. Upon cooling, the autoclave is discharged and, on the hydrogenated the residual unsaturations are determined on the hydrogenated product and a bromine number of 0.15 is obtained.

EXAMPLE 2

The procedure of Example 1 is repeated except that the autoclave is charged with 1.27 millimols of anhydrous HCl diluted in 1 ml of nor.pentane and 14 g of a C$_4$ fraction having the same composition as reported in Example 1.

The reaction is started at a temperature of +20° C. with the addition of a solution containing 1.5 millimols of AlEtCl$_2$ diluted in 10 mls of nor.pentane (molar ratio of HCl to AlEtCl$_2$=0.85).

A temperature increase up to 27° C. is experienced and the reaction is continued for 30 mins. There are obtained 7.70 g of dry product (yield 84.2%) which has an average osmometric mol wt, $\overline{Mn}$, of 643, a Br number of 34.3 and a content of Cl$_2$ (residual) of 1262 ppm.

Hydrogenation is carried out on this product according to the procedure set forth in Example 1, the residual unsaturations being subsequently determined on the hydrogenated product. A value of 0.20 is obtained for the bromine number.

EXAMPLE 3

The procedure of Example 1 is repeated except that the autoclave is charged with 0.75 millimol of anhydrous HCl diluted in 1 ml of nor.pentane and 14 g of a C$_4$ fraction having the same composition reported in Example 1.

The reaction is started at a temperature of +20° C. by the addition of a solution containing 1.5 millimol of AlEtCl$_2$ diluted in 10 mols of nor.pentane (Molar ratio of HCl to AlEtCl$_2$=0.5).

A temperature increase to as much as 26° C. is experienced and the reaction is continued for 30 mins. After discontinuation of the reaction there are obtained 4.0 g of a dry product (yield 43.8%) having an $\overline{Mn}$ of 433, a Br number of 41.7 and a content of residual Cl$_2$ of 1670 ppm. Hydrogenation is carried out on this product according to the procedure reported in Example 1 with results which are essentially equivalent.

EXAMPLE 4

The procedure reported in Example 1 is repeated except that there are charged 2.0 millimols of anhydrous HCl diluted in 1 ml of nor.pentane and 14 g of a C$_4$ hydrocarbonaceous fraction having a composition equal to that reported in Example 1.

The reaction is started at a temperature of +20° C. by introducing 1.5 millimols of AlEtCl$_2$ diluted in 10 mls of nor.pentane. (Molar ratio of HCl to AlEtCl$_2$=1.33).

The temperature rises to 29° C. and the reaction is continued for 30 mins.

There are obtained 9.1 g of a dry product (yield 100%) which has an $\overline{Mn}$ of 538, a bromine number of 36.3 and a content of residual Cl$_2$ of 1190 ppm.

EXAMPLE 5

The procedure set forth in Example 1 is repeated and there are charged to the autoclave the same quantities of C$_4$ hydrocarbonaceous fraction and of HCl.

The temperature is adjusted to 0° C. and the reaction is started with the same amount of AlEtCl$_2$ as reported in Example 1. The temperature rises to 4° C. and the reaction is allowed to proceed for 30 minutes whereafter there are obtained 5.0 g of a dry product (yield 54.7%) having an $\overline{Mn}$ of 524, a bromine number of 32.5 and a content of residual Cl$_2$ of 1080 ppm.

EXAMPLE 6

In accordance with the same procedure as set forth in Example 1 there are introduced into the autoclave the same amounts of C$_4$ hydrocarbonaceous fraction and HCl and the temperature is adjusted to 80° C. the same amount of AlEtCl$_2$ reported in Example 1 introduced into the autoclave to commence reaction.

A temperature increase to 85° C. is experienced and the reaction is allowed to proceed for 30 mins. There are obtained 6.10 g of a dry product (yield 66.8%) having an $\overline{Mn}$ of 215, a Br number of 54.5 and a content of residual Cl$_2$ to 1850 ppm.

EXAMPLE 7

In accordance with the same procedure as set forth in Example 1 there are charged into the autoclave 4.5. millimols of anhydrous HCl diluted in 1 ml of nor.pentane and 14.0 g of a C$_4$ hydrocarbonaceous fraction having a composition equal to that reported in Example 1.

The temperature is stabilized to 20° C. and the reaction is started by introducing 1.5 millimols of AlEt$_3$ diluted in 10 mls of nor.pentane (Molar ratio of HCl to AlEt$_3$=3.0).

The temperature rises to 30° C. and there are obtained 7.82 g of a dry product (yield 85.6%) having an $\overline{Mn}=405$, a bromine number of 39.5 and a content of residual $Cl_2$ of 1058 ppm.

EXAMPLE 8

In accordance with the same procedure as set forth in Example 1 there are introduced into the autoclave 3.0 millimols of anhydrous HCl diluted in 1 ml of nor.pentane and 14.0 g of a $C_4$ hydrocarbonaceous fraction having the same composition as reported in Example 1.

The temperature is stabilized to 20° C. and there introduced into the autoclave in order to start the reaction 1.5 millimols of $AlEt_2Cl$ diluted in 10 mls of nor.-pentane.

The molar ratio of HCl to $AlEt_2Cl$ is 2.0.

The temperature rises to 31° C., the reaction is allowed to proceed for 30 mins. and there are obtained 8.90 g of a dry oligomer (yield 97.4%) having an $\overline{Mn}$ of 363, a bromine number of 40.4 and a content of residual $Cl_2$ to 1080 ppm.

EXAMPLE 9

In accordance with the procedure as set forth in Example 1 there are introduced 2.25 millimols of anhydrous HCl diluted in 1 ml of nor.pentane and 14.0 g of a $C_4$ hydrocarbonaceous fraction having the same composition as reported in Example 1.

The temperature is stabilized to 20° C. and the reaction is started by adding 1.5 millimol of AlEt sesquichloride diluted in 10 mls of nor.pentane, the molar ratio of HCl to AlEt sesquichloride being 1.5.

The temperature rises to 29° C., the reaction is continued for 30 mins. and there are obtained 8.5 g of a dry product (yield 89.8%) having an $\overline{Mn}$ of 450, a bromine number of 39.5 and a content of residual $Cl_2$ of 1120 ppm.

We claim:

1. A method for the preparation of oligomers from alpha-olefins comprising polymerizing said alpha-olefins in the presence of a catalytic system composed of:
   (a) an organic metallic compound of aluminum having the following general formula:

$R_mAlX_{3-m}$ wherein X is a halogen atom, R is hydrogen or a monovalent radical selected from the group consisting of alkyl, aryl, cycloalkyl, aralkyl, alkaryl, alkoxyl and ester radicals having from 1 to 12 carbon atoms, and m is between 1 and 3; and
   (b) a compound having the formula HX in which X is halogen and which is capable of reacting with the compounds defined above under (a) to produce a catalytic species capable of starting the polymerization.

2. A method according to claim 1 wherein the polymerization is carried out in a homogeneous phase in the presence of a solvent selected from the group consisting of hydrocarbons having between 3 and 12 carbon atoms and their halogen substituted derivatives.

3. A method according to claim 1 wherein the polymerization is carried out without any solvent being present.

4. A method according to claim 1 wherein the polymerization is carried out with a molar ratio of (a) to (b) between 0.1 and 5 to 1.0.

5. A method according to claim 1 wherein the polymerization is carried out at a temperature between −30° C. and +100° C.

6. A method for the removal of unsaturations from oligomers obtained according to claim 1 comprising the step of contacting said oligomers with a hydrogenation catalyst at a temperature of from 150° C. to 300° C. under a partial hydrogen pressure between 20 atmospheres and 150 atmospheres and optionally flowing the product thus obtained through a bed of siliceous adsorbent earths at a temperature between 50° C. and 100° C.

7. Saturated oligomeric products obtained according to the method of claim 6.

8. A method according to claim 2 wherein the polymerization is carried out with a molar ratio of (a) to (b) between 0.1 and 5 to 1.0.

9. A method according to claim 2 wherein the polymerization is carried out at a temperature between −30° C. and +100° C.

10. A method according to claim 3 wherein the polymerization is carried out with a molar ratio of (a) to (b) between 0.1 and 5 to 1.0.

11. A method according to claim 3 wherein the polymerization is carried out at a temperature between −30° C. and +100° C.

12. A method according to claim 4 wherein the polymerization is carried out at a temperature between −30° C. and −100° C.

13. A method for the removal of unsaturation from oligomers obtained according to claim 2 comprising the step of contacting said oligomers with a hydrogenation catalyst at a temperature of from 150° C. to 300° C. under a partial hydrogen pressure between 20 atmospheres and 150 atmospheres and optionally flowing the product thus obtained through a bed of siliceous adsorbent earths at a temperature between 50° C. and 100° C.

14. Saturated oligomeric products obtained according to the method of claim 13.

15. A method for the removal of unsaturation from oligomers obtained according to claim 3 comprising the step of contacting said oligomers with a hydrogenation catalyst at a temperature of from 150° C. to 300° C. under a partial hydrogen pressure between 20 atmospheres and 150 atmospheres and optionally flowing the product thus obtained through a bed of siliceous adsorbent earths at a temperature between 50° C. and 100° C.

16. Saturated oligomeric products obtained according to the method of claim 15.

17. A method for the removal of unsaturations from oligomeric products obtained according to claim 4 comprising the step of contacting said oligomers with a hydrogenation catalyst at a temperature of from 150° C. to 300° C. under a partial hydrogen pressure between 20 atmospheres and 150 atmospheres and optionally flowing the product thus obtained through a bed of siliceous adsorbent earths at a temperature between 50° C. and 100° C.

18. Saturated oligomeric products obtained according to the method of claim 17.

19. A method for the removal of unsaturations from oligomeric products obtained according to claim 5 comprising the step of contacting said oligomers with a hydrogenation catalyst at a temperature of from 150° C. to 300° C. under a partial hydrogen pressure between 20 atmospheres and 150 atmospheres and optionally flowing the product thus obtained through a bed of siliceous adsorbent earths at a temperature between 50° C. and 100° C.

20. Saturated oligomeric products obtained according to the method of claim 19.

21. A method according to claim 1 wherein the polymerization is carried out with a molar ratio of (a) to (b) between 0.5 and 3 to 1.0.

22. A method according to claim 1 wherein the polymerization is carried out at a temperature between −10° C. and +80° C.

23. A method according to claim 2 wherein the polymerization is carried out with a molar ratio of (a) to (b) between 0.5 and 3 to 1.0.

24. A method according to claim 2 wherein the polymerization is carried out at a temperature between −10° C. and +80° C.

25. A method according to claim 3 wherein the polymerization is carried out with a molar ratio of (a) to (b) between 0.5 and 3 to 1.0.

26. A method according to claim 3 wherein the polymerization is carried out at a temperature between −10° C. and +80° C.

27. A method according to claim 4 wherein the polymerization is carried out between −10° C. and +80° C.

* * * * *

UNITED STATES PATENT AND TRADEMARK OFFICE
CERTIFICATE OF CORRECTION

PATENT NO. : 4,197,420
DATED : April 8, 1980
INVENTOR(S) : Giuseppe Ferraris et al.

It is certified that error appears in the above—identified patent and that said Letters Patent is hereby corrected as shown below:

On the Title Page insert:

-- Assignee: ANIC S.p.A., Palermo, Italy --.

Signed and Sealed this

Twenty-fourth Day of June 1980

[SEAL]

*Attest:*

SIDNEY A. DIAMOND

*Attesting Officer*     *Commissioner of Patents and Trademarks*